United States Patent [19]

Liff

[11] 4,183,898

[45] Jan. 15, 1980

[54] LIQUID BASE MAKEUP COMPOSITION

[76] Inventor: Lawrence J. Liff, 6502 N. Central #A-101, Phoenix, Ariz. 85012

[21] Appl. No.: 909,576

[22] Filed: May 25, 1978

[51] Int. Cl.² ............................................. A61K 7/021
[52] U.S. Cl. ...................................... 424/63; 424/362
[58] Field of Search .................. 424/63, 149, 362, 363

[56] References Cited

U.S. PATENT DOCUMENTS

| | | | |
|---|---|---|---|
| 3,351,527 | 11/1967 | Apat et al. ............................ | 424/362 |
| 3,439,088 | 4/1969 | Edman ............................. | 424/358 X |
| 3,591,515 | 7/1971 | Lovely et al. ......................... | 424/149 |
| 3,764,707 | 10/1973 | Habersberger ........................ | 424/363 |
| 3,818,105 | 6/1974 | Coopersmith et al. .............. | 424/358 |
| 3,870,790 | 3/1975 | Lowey et al. ......................... | 424/362 |
| 3,978,235 | 8/1976 | Schiro .................................. | 424/149 |

*Primary Examiner*—Dale R. Ore
*Attorney, Agent, or Firm*—Woodling, Krost, Granger & Rust

[57] ABSTRACT

A liquid base makeup composition primarily for use by children to simulate various things, for example, blood. This composition is relatively inexpensive and is quite safe for children's use. The composition consists essentially of 96.48% water, 2.0% cellulose, 0.15% ethyl and propylparaben, 1.34% chlorine dioxide and 0.03% phosphoric acid.

4 Claims, No Drawings

LIQUID BASE MAKEUP COMPOSITION

The present application discloses a liquid base makeup composition which can be used for many purposes; however, the most common use of the composition disclosed herein is for children to use as make believe blood.

The present invention discloses a composition which is ideally suited for the above mentioned purpose because it is relatively inexpensive to manufacture and therefore can be sold to the ultimate consumer at a reasonable price; it is quite realistic in appearance and when made in accordance with the present invention it is safe for use by children whether it is accidentally taken internally or if used in its intended purpose and applied to the exterior of the body.

Historically there has always been some kind of liquid makeup used to simulate blood which was used primarily for stage purposes and in more recent years for use in movies and for television purposes. Examples of make believe blood compositions include sugar-water-base materials normally with food coloring added.

Modern technology has developed very expensive compositions to simulate the stage blood which is now used extensively in the entertainment industry. It should be kept in mind that these compositions of matter are extremely expensive and do not lend themselves to the purpose of providing an inexpensive liquid base makeup composition which can be used by children as well as others.

Children historically have used play blood of all kinds in make believe games and the number one historical product for this use has been ketchup. This particular material meets one of the afore-mentioned criteria in that it is quite inexpensive; however, it lacks a realistic appearance and for that purpose is relatively unsatisfactory. Ketchup is also a food product which will spoil, develop bacteria and will cause many allergetic reactions.

Several criteria in addition to those enumerated above must be met in order to accomplish the desired end result and these include a product consistency whereby the liquid base composition will not be extremely runny and it must be easily washed off the skin or any other material that it comes in contact with. It also should not stain various fabric materials.

It is also necessary that the composition when exposed to air, start in a liquid state as a reddish-brown color and end up in the coagulated state as a brownish-red color thereby closely simulating real blood.

It is also necessary that the composition when used for the above recited purposes be essentially free of any supportive pathogenic bacteria in that it should be essentially non-toxic and safe when used either externally or if accidentally ingested.

With these thoughts in mind the present disclosure relates to a liquid base makeup composition which meets the above referred to criteria, namely it is inexpensive to manufacture and therefore is relatively inexpensive to the ultimate consumer; it is a safe material whether applied externally as it is intended or is accidentally ingested; and it is quite realistic appearing when accomplishing its intended function. The present invention as disclosed herein is relatively critical with respect to the materials which go into the composition of matter which is claimed and it is essentially critical that all of the method steps involved in making the composition be rigidly adhered to.

With the above requirements clearly in mind the basic liquid base composition which can be expanded for use in multiple makeup uses is given immediately hereinbelow. The composition has been described in connection with the making of a 600 gallon batch.

TABLE I

|  | Weight (kg) | % |
|---|---|---|
| Water | 2177.3 | 96.48 |
| Hydroxypropylmethylcellulose (Methocel, 65 HG 4000) | 45.36 | 2.00 |
| Propylparaben | 1.134 | 0.05 |
| Ethylparaben | 2.268 | 0.10 |
| Chlorine dioxide 2% (Stabilized) | 30.24 | 1.34 |
| Phosphoric acid (Food grade) | 0.757 | 0.03 |
| Total | 2556.06 | 100.00 |

In the formulation given immediately hereinabove the water acts essentially as a carrier for all of the ingredients. The hydroxypropylmethylcellulose is the agent that provides a thickening of the formulation and when the composition is applied in its ultimate use, water evaporates and the thinned material which remains is the cellulose material. The cellulose material is also the bulk agent that allows the formulation to act as an adhesive.

The ethylparaben and propylparaben, the stabilized chlorine dioxide and the phosphoric acid accomplish the function of protecting the formulation from bacteria and help give it a long shelf life.

The above disclosed liquid base formulation is then normally formulated into either a red appearing makeup blood or a green appearing makeup blood, or used as a makeup adhesive to attach and/or hold cotton and/or other prosthetic devices to the face and/or other parts of the body. When being used in the last application mentioned above it may be used in an uncolored form or it may have almost any color added to it depending on the requirements of the visual effect. Also when being used in this application, when cotton is used, this liquid base makeup formulation can be applied over the cotton to help shape it. This causes the cotton to become firm once the water has evaporated from the formulation. When the formulation is colored and used in this way it becomes a regular makeup base. In order to accomplish this, various artifical colorants are added to each 600 gallon batch of the liquid base formulation. The amounts, color blends, and intensities of these added dyes are determined by the intended end use for that 600 gallon batch of liquid base makeup composition. The color standards for these dye materials are set by the World Health Organization. These colors are listed in the Code of Federal Regulations, Title 21, Parts 1-9. The amount of colorant used is on the order of 0.1% (0.001) of the total batch weight.

The basic liquid formulation is comprised of the water, cellulose material, propylparaben, ethylparaben, stabilized chlorine dioxide and food grade phosphoric acid in the amounts indicated. If a red blood effect is desired, it is only necessary to incorporate into the basic liquid formulation red colorant materials for the red blood and if a green blood effect is desired, green colorant materials are added and the red materials are omitted from the basic liquid formulation.

The blood makeup composition enumerated hereinabove uniquely satisfies the criteria for a satisfactory product in that the material when utilized has a consistency closely approximating actual blood thereby giving a realistic effect when used. Because of the relatively inexpensive ingredients it can be sold to the ultimate consumers (usually children) at a relatively inexpensive price. Also because of the ingredients that go into this unique composition it is non-toxic and as a result it is not harmful when used either in its intended purpose externally or in the event the composition is accidentally ingested.

The method steps that are involved in making the liquid base makeup composition are extremely important and critical and if altered even in the slightest manner the formulation will be either too thick or too thin. It is also possible, if the following steps are not strictly adhered to, that the formulation may lose its bacteriological protection altogether.

The method steps that are involved in the making of the liquid base composition are given hereinbelow.

1. Clean, disinfect and rinse all mixing equipment.
2. Place 132.3 Kg. of 180° F. water into a mixing container.
3. Add all ethylparaben and propylparaben and agitate for 5 minutes.
4. Add all phosphoric acid and 11.34 Kg. stabilized chlorine dioxide and agitate for 10 minutes.
5. Add all dye and colorant materials and agitate 10 minutes.
6. Continue agitation and begin to add 226.8 Kg. 180° F. water and slowly add the hydroxypropylmethylcellulose at the same time.
7. Let solution agitate for about 15 minutes.
8. Add 1,818.2 Kg. of cold water and continue to agitate.
9. Add 11.34 Kg. of stabilized chlorine dioxide and agitate aproximately 2 hours.
10. Add 7.56 Kg. of stabilized chlorine dioxide approximaterly 10–16 hours after completing step #9 and agitate 2-3 hours.
11. Agitate periodically as long as the composition remains in the mixing container.

As stated, it is necessary to follow the method steps critically and to the letter otherwise the criteria enumerated hereinabove for a satisfactory liquid base composition will not be achieved.

Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. A liquid base formulation for multiple makeup uses consisting of 96.48% water; 2.0% cellulose; 0.15% of ethylparaben and propylparaben; 1.34% chlorine dioxide; and 0.03% phosphoric acid.

2. A liquid base makeup composition as claimed in claim 1 wherein said cellulose is hydroxypropylmethylcellulose.

3. A liquid base makeup composition as claimed in claim 2 wherein a colored makeup is produced by the addition of artificial coloring materials.

4. The method of making a 2556.06 Kg batch of a liquid base makeup composition consisting of the steps of adding about 132.3 Kg. of water at about 180° F. to a container;

adding about 2.268 Kg. of ethylparaben and about 1.134 Kg. of propylparaben to said water with about 5 minutes of agitation;

adding about 0.757 Kg. of phosphoric acid and about 11.34 Kg. of stabilized chlorine dioxide with about 10 minutes of agitation;

adding about 45.36 Kg. of a cellulose material along with 226.8 Kg. of water at 180° F. with constant agitation;

continuing the agitation for about 15 minutes;

adding about 1,818.2 Kg. of cold water with continued agitation;

adding about 11.34 Kg. of stabilized chlorine dioxide and agitating for about 2 hours;

adding about 7.56 Kg. of stabilized chlorine dioxide about 10 to 16 hours after agitating step just immediately referred to above and agitating for about 2 to 3 hours; and thereafter agitating periodically.

* * * * *